US00PP22979P2

(12) United States Plant Patent
Hachmann

(10) Patent No.: US PP22,979 P2
(45) Date of Patent: Aug. 21, 2012

(54) *ILEX* PLANT NAMED 'HECKENZWERG'

(50) Latin Name: *Ilex aquifolium*
Varietal Denomination: Heckenzwerg

(76) Inventor: Holger Hachmann, Barmstedt (DE)

( * ) Notice: Subject to any disclaimer, the term of this patent is extended or adjusted under 35 U.S.C. 154(b) by 55 days.

(21) Appl. No.: 12/928,569

(22) Filed: Dec. 14, 2010

(51) Int. Cl.
*A01H 5/00* (2006.01)

(52) U.S. Cl. ..... Plt./247
(58) Field of Classification Search ..... Plt./247
See application file for complete search history.

*Primary Examiner* — June Hwu
(74) *Attorney, Agent, or Firm* — C. A. Whealy

(57) ABSTRACT

A new and distinct cultivar of *Ilex* plant named 'Heckenzwerg', characterized by its compact, upright and broadly inverted triangular plant form; freely branching habit; dense and bushy growth habit; glossy dark green-colored leaves with recurved apices and spinose margins; and good garden performance.

2 Drawing Sheets

Botanical designation: *Ilex aquifolium.*
Cultivar denomination: 'HECKENZWERG'.

BACKGROUND OF THE INVENTION

The present Invention relates to a new and distinct *Ilex* plant, botanically known as *Ilex aquifolium*, and hereinafter referred to by the name 'Heckenzwerg'.

The new *Ilex* plant is the product of an open pollination in 1990 of *Ilex aquifolium* 'Myrtifolia', not patented, as the female, or seed, parent with an unknown selection of *Ilex aquifolium* as the male, or pollen, parent. The new *Ilex* plant was discovered by the Inventor in 1995 from within the progeny of the stated open pollination in an outdoor nursery in Barmstedt, Germany.

Asexual reproduction of the *Ilex* plant by cuttings in Barmstedt, Germany since 2000 has shown that the unique features of this new *Ilex* plant are stable and reproduced true to type in successive generations of asexual reproduction.

SUMMARY OF THE INVENTION

Plants of the new *Ilex* have not been observed under all possible environmental conditions. The phenotype may vary somewhat with variations in environment such as temperature and/or light intensity without, however, any variance in genotype. The following traits have been repeatedly observed and are determined to be the unique characteristics of 'Heckenzwerg'. These characteristics in combination distinguish 'Heckenzwerg' as a new and distinct *Ilex* plant:

1. Compact, upright and broadly inverted triangular plant form.
2. Freely branching habit; dense and bushy growth habit.
3. Glossy dark green-colored leaves with recurved apices and spinose margins.
4. Good garden performance.

Plants of the new *Ilex* can be compared to plants of the female parent, 'Myrtifolia'. Plants of the new *Ilex* differ from plants of 'Myrtifolia' in the following characteristics:

1. Plants of the new *Ilex* are more compact and grow slower than plants of 'Myrtifolia'.
2. Plants of the new *Ilex* are denser than and not as open as plants of 'Myrtifolia'.

3. Plants of the new *Ilex* have broader and lighter green-colored leaves than plants of 'Myrtifolia'.

Plants of the new *Ilex* can be compared to the plants of *Ilex* 'Xia Xiang', disclosed in U.S. Plant Pat. No. 10,526. Plants of the new *Ilex* differ primarily from plants of 'Xia Xiang' in plant form and growth habit.

BRIEF DESCRIPTION OF THE PHOTOGRAPHS

The accompanying colored photographs illustrate the overall appearance of the new *Ilex* plant showing the colors as true as it is reasonably possible to obtain in colored reproductions of this type. Colors in the photographs may differ slightly from the color values cited in the detailed botanical description which accurately describe the colors of the new *Ilex* plant.

The photograph on the first sheet comprises a side perspective view of a typical plant of 'Heckenzwerg' grown in a container.

The photograph on the second sheet is a close-up view of a typical plant of 'Heckenzwerg'.

DETAILED BOTANICAL DESCRIPTION

The aforementioned photographs and following observations and measurements describe plants grown in two-liter containers during the winter in an outdoor nursery in Boskoop, The Netherlands and under commercial production conditions. During the production of the plants, day temperatures ranged from 4° C. to 10° C. and night temperatures ranged from −4° C. to 3° C. Plants used for the photographs and description were 2.5 years old. In the following description, color references are made to The Royal Horticultural Society Colour Chart, 2007 Edition, except where general terms of ordinary dictionary significance are used.

Botanical classification: *Ilex aquifolium* 'Heckenzwerg'.

Parentage:

*Female, or seed, parent.*—*Ilex aquifolium* 'Myrtifolia', not patented.

*Male, or pollen, parent.*—Unknown selection of *Ilex aquifolium*, not patented.

Propagation:

*Type.*—By cuttings.

*Time to initiate roots, summer*.—About three weeks at temperatures of 30° C.

*Time to initiate roots, winter*.—About four weeks at temperatures of 5° C.

*Time to produce a rooted young plant*.—About one year at temperatures of 20° C. to 25° C.

*Root description*.—Fine, slightly fibrous; color, close to N167B.

*Rooting habit*.—Moderately freely branching; medium density.

Plant description:

*Plant form and growth habit*.—Perennial evergreen shrub; compact, upright and broadly inverted triangular plant form; vigor, low to moderate.

*Branching habit*.—Freely branching habit; dense and bushy growth habit with about 14 primary lateral branches developing per plant.

*Plant height*.—About 18.6 cm.

*Plant diameter, area of spread*.—About 19.9 cm.

*Lateral branch description*.—Length: About 8.7 cm. Diameter: About 3.5 mm. Internode length: About 6 mm. Strength: Strong. Texture: Smooth, glabrous. Color, young stems: Close to N186C and 200A. Color, mature stems: Close to 147B.

*Leaf description*.—Arrangement: Alternate, simple. Length: About 4 cm. Width: About 1.4 cm. Shape: Narrowly elliptic to narrowly ovate. Apex: Sharply acuminate; recurved. Base: Attenuate. Margin: Spinose; about 14 spines per leaf; about 2.5 mm in length. Texture, upper and lower surfaces: Smooth, glabrous; thick and leathery. Luster, upper surface: Glossy. Luster, lower surface: Matte, dull. Venation pattern: Pinnate. Color: Developing leaves, upper surface: Close to 146A. Developing leaves, lower surface: Close to 146C. Fully expanded leaves, upper surface: Darker than 147A and N189A; spines, close to 151C to 151D; venation, close to N189A. Fully expanded leaves, lower surface: Close to 146B; spines, close to 151C to 151D; venation, close to 146B. Petiole: Length: About 5 mm. Diameter: About 1 mm. Texture, upper and lower surfaces: Smooth, glabrous. Color, upper and lower surfaces: Close to 144A.

Flower description: Flower initiation and development have not been observed on plants of the new *Ilex*.

Garden performance: Plants of the new *Ilex* have been observed to have good garden performance and to tolerate rain, wind, high temperatures of about 35° C. and to be hardy to USDA Hardiness Zone 5.

Disease/pest resistance: Plants of the new *Ilex* have not been observed to be resistant to pathogens and pests common to *Ilex*.

It is claimed:

1. A new and distinct cultivar of *Ilex* plant named 'Heckenzwerg' as illustrated and described.

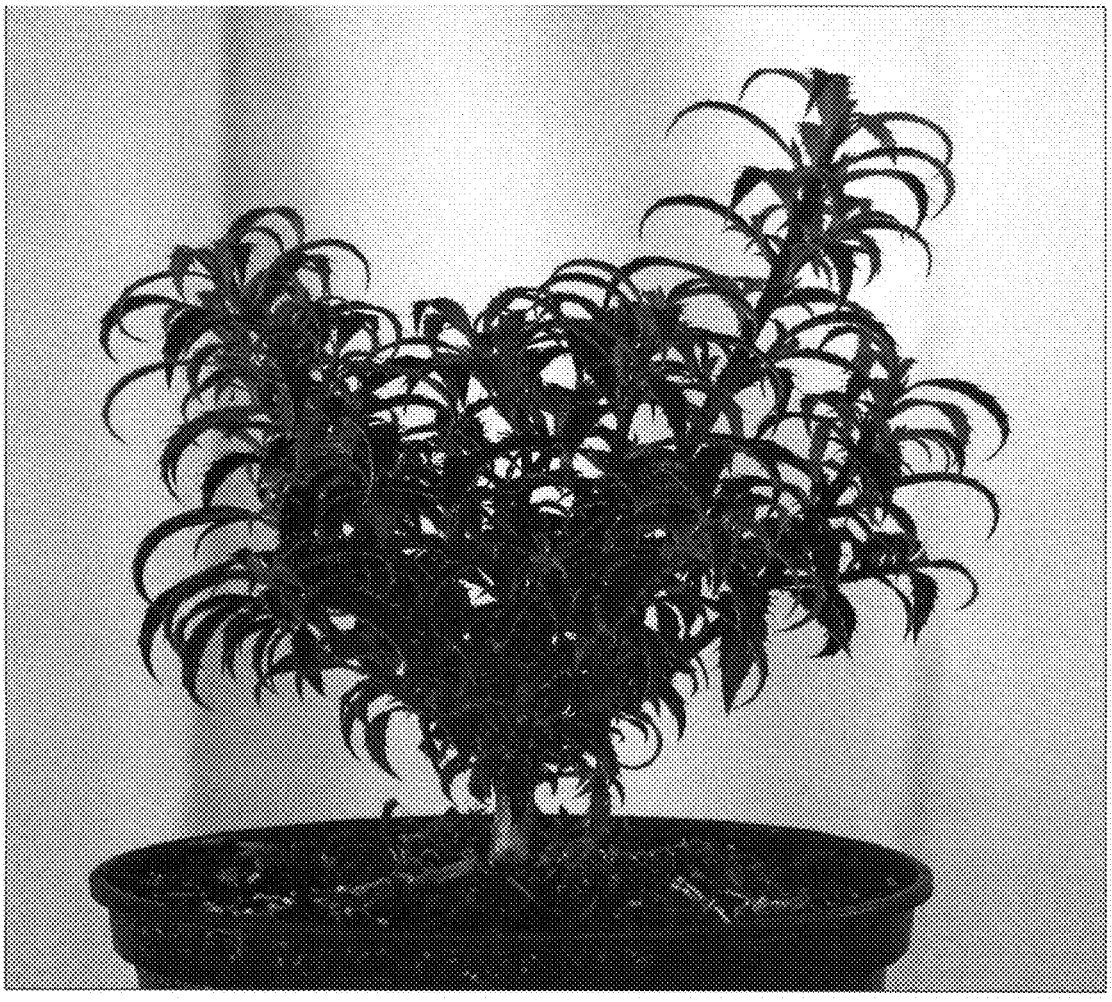

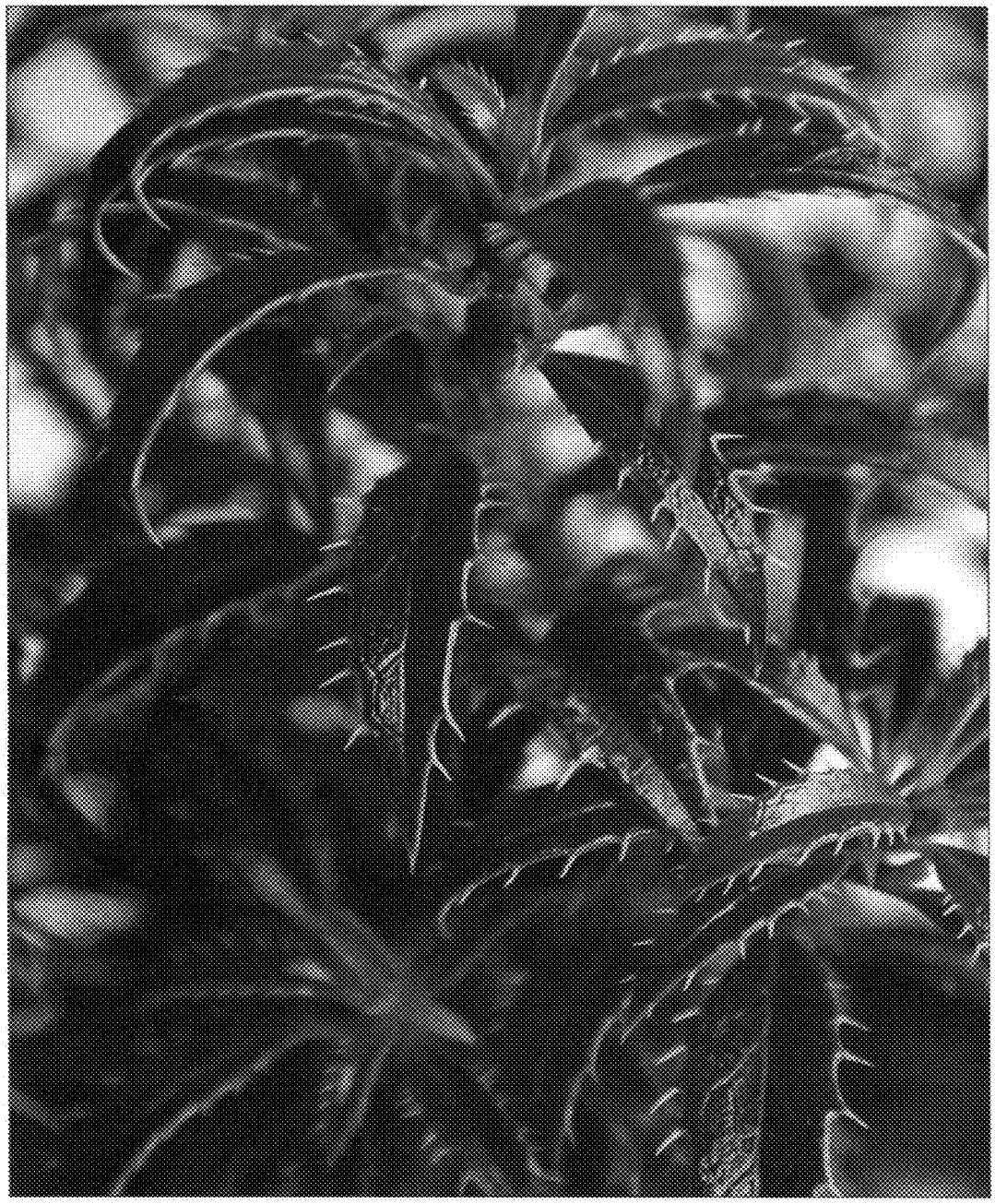

* * * * *